（12）United States Patent
van Donkelaar et al.

(10) Patent No.: US 10,765,521 B2
(45) Date of Patent: Sep. 8, 2020

(54) BIOMIMETIC FUNCTIONAL AND REGENERATIVE CARTILAGE IMPLANT

(71) Applicants: Technische Universiteit Eindhoven, Eindhoven (NL); RWTH Aachen, Aachen (DE)

(72) Inventors: Corrinus Cornelis van Donkelaar, Eindhoven (NL); Keita Ito, Helmond (NL); Tim Bolle, Aachen (DE)

(73) Assignees: Technische Universiteit Eindhoven, Eindhoven (NL); RWTH Aachen, Aachen (DE)

( * ) Notice: Subject to any disclaimer, the term of this patent is extended or adjusted under 35 U.S.C. 154(b) by 0 days.

(21) Appl. No.: 16/332,253

(22) PCT Filed: Oct. 19, 2017

(86) PCT No.: PCT/EP2017/076719
§ 371 (c)(1),
(2) Date: Mar. 11, 2019

(87) PCT Pub. No.: WO2018/073347
PCT Pub. Date: Apr. 26, 2018

(65) Prior Publication Data
US 2019/0231534 A1 Aug. 1, 2019

Related U.S. Application Data

(60) Provisional application No. 62/410,812, filed on Oct. 20, 2016.

(51) Int. Cl.
*A61F 2/30* (2006.01)
*A61L 27/52* (2006.01)
(Continued)

(52) U.S. Cl.
CPC .......... *A61F 2/30756* (2013.01); *A61L 27/50* (2013.01); *A61L 27/52* (2013.01);
(Continued)

(58) Field of Classification Search
CPC ....................................................... A61F 2/30
See application file for complete search history.

(56) References Cited

U.S. PATENT DOCUMENTS

2005/0287187 A1    12/2005   Mansmann
2009/0088846 A1    4/2009   Myung
(Continued)

FOREIGN PATENT DOCUMENTS

WO   WO2005087239    9/2005
WO   WO2006113642    10/2006
(Continued)

*Primary Examiner* — Matthew W Schall
(74) *Attorney, Agent, or Firm* — Lumen Patent Firm

(57) ABSTRACT

An artificial cartilage is provided whereby a fixed negative charged hydrogel has been infused within a restrictive swelling network, which limits and restricts the thickness of the artificial cartilage. At least 60% of the volume of the artificial cartilage is composed of the restricted and swollen hydrogel. The restrictive swelling network restricts the hydrogel to swell not more than 10% with respect to its maximum swelling capacity, i.e. a swelling capacity to swell 10-fold more is retained. The hydrogel within the restrictive swelling network has an equilibrium stiffness between 0.5 and 2 MPa to resist external loads applied to the top surface layer or the bottom surface layer of the artificial cartilage. The hydrogel has a fixed negative charge density of −0.17 to −0.23 mEg/ml and is capable of swelling between 2-15 times compared to the volume of the hydrogel without being restricted.

6 Claims, 6 Drawing Sheets

(51) Int. Cl.
  *A61L 27/50* (2006.01)
  *A61L 27/58* (2006.01)
(52) U.S. Cl.
  CPC .............. *A61F 2002/30761* (2013.01); *A61F 2002/30766* (2013.01); *A61L 27/58* (2013.01)

(56) References Cited

U.S. PATENT DOCUMENTS

2015/0238318 A1 8/2015 McCullen
2016/0228604 A1 8/2016 Mann

FOREIGN PATENT DOCUMENTS

| WO | WO2007030811 | 3/2007 |
| WO | WO2008026928 | 3/2008 |
| WO | WO2008026929 | 3/2008 |
| WO | WO2012128631 | 9/2012 |
| WO | WO2017041109 | 3/2017 |

BIOMIMETIC FUNCTIONAL AND REGENERATIVE CARTILAGE IMPLANT

CROSS-REFERENCE TO RELATED APPLICATIONS

This application is a 371 of PCT application PCT/EP2017/076719 filed Oct. 19, 2017. PCT application PCT/EP2017/076719 claims the benefit of U.S. Provisional application 62/410,812 filed Oct. 20, 2016.

FIELD OF THE INVENTION

This invention relates to artificial cartilage implants.

BACKGROUND OF THE INVENTION

Defective articular cartilage frequently occurs, is painful and requires treatment. Current clinical solutions have average success rates of 40-80%. Several of these approaches are based on replacement of damaged cartilage by an implant while others aim to regenerate native cartilage. Although some approaches are effective for specific defects in certain patients, a general solution for cartilage replacement/regeneration does not yet exist and each approach comes with significant limitations.

Limitations of available implants are that their mechanical properties do not mimic those of natural cartilage, create damaging high stress/strains in adjacent and opposing cartilage, their size is predefined and cannot be adjusted intra-operatively, and they do not allow post-operative MRI.

Regenerative techniques, e.g. micro-fracturing and (M)ACI (Matrix-associated Autologous Chondrocyte Implantation), are not immediately load-bearing and only successful in young patients with considerable regenerative potential, while transplantation techniques, such as mosaic-plasty, have the disadvantage that it requires damaging healthy cartilage at another location in the joint.

The present invention is intended to provide a general and functional solution for the repair of defective cartilage.

SUMMARY OF THE INVENTION

The present invention provides an artificial cartilage whereby a fixed negative charged hydrogel has been infused within a restrictive swelling network. The restrictive swelling network is a spacer network of filaments with a top surface layer, a bottom surface layer, and some of the filaments crossing in a middle area layer between both the top and bottom surface layers limiting and restricting the maximum distance between both the top and bottom surface layers. At least 60% of the volume of the artificial cartilage is composed of the restricted and swollen fixed negative charged hydrogel. The maximum distance between both the top and bottom surface layers is between 0.8-6 mm.

The restrictive swelling network restricts the fixed negative charged hydrogel to swell not more than 10% with respect to the maximum swelling capacity of the fixed negative charged hydrogel without being constraint by the restrictive swelling network. i.e. a swelling capacity to swell 10-fold more is retained. In another embodiment, the restrictive swelling network restricts the fixed negative charged hydrogel to swell not more than 5% (or at most 5%) with respect to the maximum swelling capacity of the fixed negative charged hydrogel without being constraint by the restrictive swelling network. i.e. a swelling capacity to swell 20-fold more is retained.

The fixed negative charged hydrogel within the restrictive swelling network has an equilibrium stiffness between 0.5 and 2 MPa to resist external loads applied to the top surface layer or the bottom surface layer of the artificial cartilage. The fixed negative charged hydrogel has a fixed negative charge density of −0.17 to −0.23 mEg/ml and is capable of swelling between 2-15 times compared to the volume of the hydrogel without being restricted.

In one embodiment, the middle area layer of the spacer network of filaments defines an interconnecting pile of filaments restricting the maximum distance between the top surface layer and the bottom surface layer, with a pile density of at least 10 filaments/cm$^2$, with a pile angle between 45-90 degrees defined with reference to either the top or bottom surface layer, and with an elasticity of the spacer network of filaments between 100 kPa and 10 MPa defined in a load direction perpendicular to either the top or bottom surface layer. The maximum pile density is limited to ensure at least 60% of the volume of the artificial cartilage is composed of the restricted and swollen fixed negative charged hydrogel.

Fixed negative charges refers to electrically negatively charged groups that are inherent, covalently bound parts of the molecules that constitute the hydrogel. Typically, the monomers that constitute the (co)polymeric gel contain carboxylated (~COO$^-$), sulphated (~SO$_4^-$), or thiol (S) groups.

Filaments may be synthetic or natural, mono-, multifilament or staple fibres and include: Synthetic (polycaprolactone (PCL), Polylactic acid (PLA, PLLA, PDLA), polylacto-co-glycolic acid (PLGA), polytetrafluoroethylene (PTFE), polydioxone (PDO), polyglycolic acid (PGA), polyvinylalcohol (PVA), polyethylene oxide (PEO), polyethyleneglycol (PEG)), polyethylenterephthalat (PET), polypropylen (PP), polyvinylidenfluorid (PVDF)); Natural fibers (Collagen, gelatin, elastin, chitosan, silk fibroin, alginate, fibrin); as well as any combination as blends or co-polymers of the above materials.

Examples are hydrogels based on Methacrylate (MA), including MMA, polymethacrylic acid-co-acrylamide (PMMA), 2-hydroxyethylmethacrylate (pHEMA), N, N-dimethylacrylamide (DMA), ethylene glycol dimethacrylate, poly(hydroxyl methacrylate-co-methacrylic acid); Chondroitin Sulphate (CS), including CS-MA and CS-analogue gels; Polyethylene glycol (PEG), including polyethylene oxide (PEO), polyoxyethylene (POE) and polyrotaxane gel. These hydrogels may also be blends or combinations of the above materials, or used in combination with other molecules. They may be degradable or non-degradable, and may be reinforced using nanocomposites, double network hydrogels, crosslinks, slip-links, or supramolecular approaches.

Embodiments of the invention provide a functional solution for the repair of defective cartilage, which:
 provides immediate functional mechanical load-bearing based on a biomimetic mechanism,
 allows tailoring of the load-bearing properties to patient-specific requirements,
 can be used to treat any size defect, and can be adjusted intra-operatively to the size of the defect,
 allows post-operative MRI, and/or
 may be used to stimulate regeneration.

BRIEF DESCRIPTION OF THE DRAWINGS

FIG. 1 shows according to an exemplary embodiment of the invention a spacer network of filaments 100 of the artificial cartilage. The spacer network of filaments 100 shows a top surface layer 110, a bottom surface layer 120, and filaments crossing in a middle area layer 130 between both the top and bottom surfaces layers limiting and restricting the maximum distance between both the top and bottom surface layers. In this example, the filaments in the middle area layer 130 shows a pile density of 30 filaments/cm$^2$, given that there are 6 piles per cm in the course direction and 5 piles per cm in the wale direction.

Figure 1:
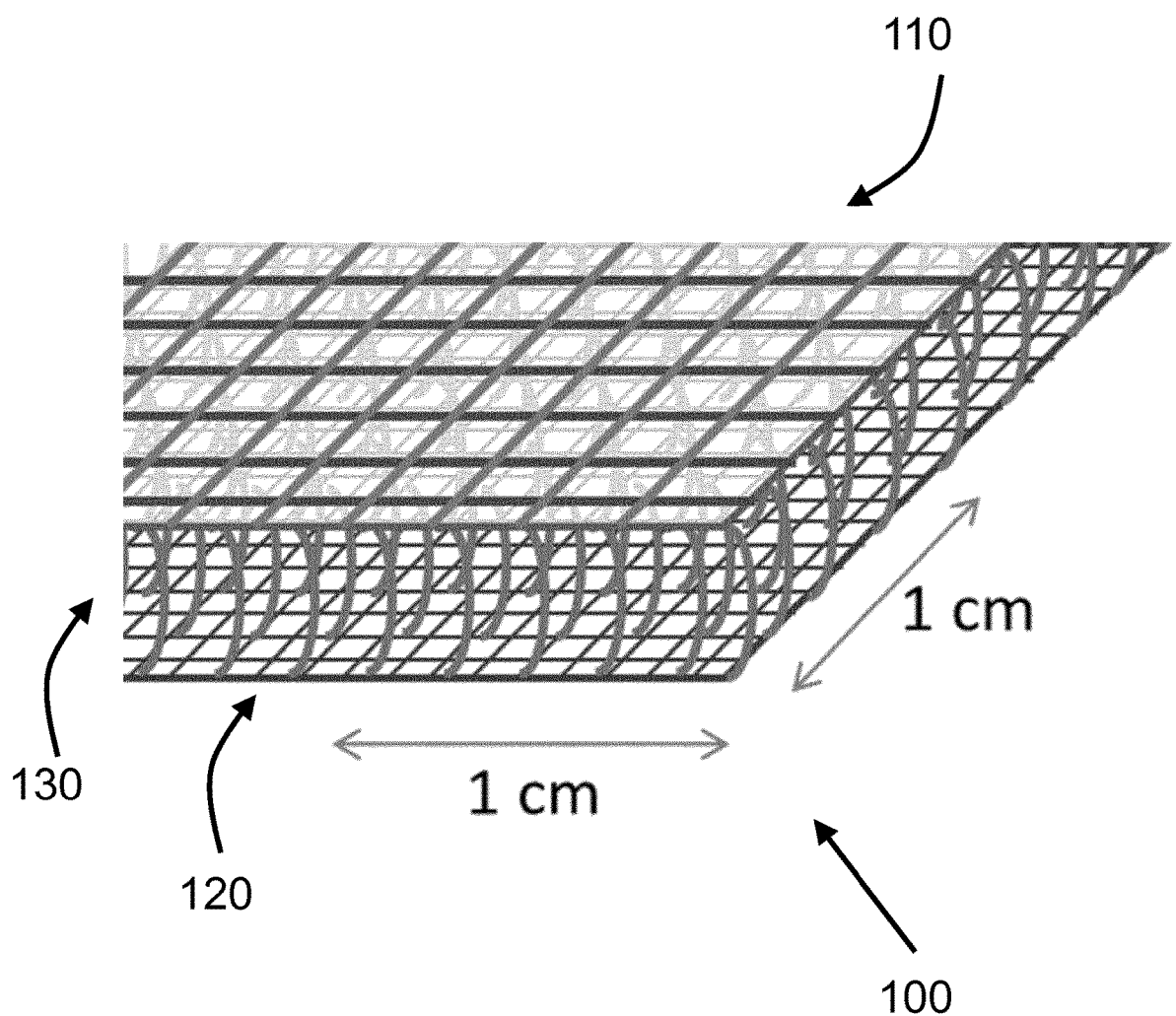
Figure 2:
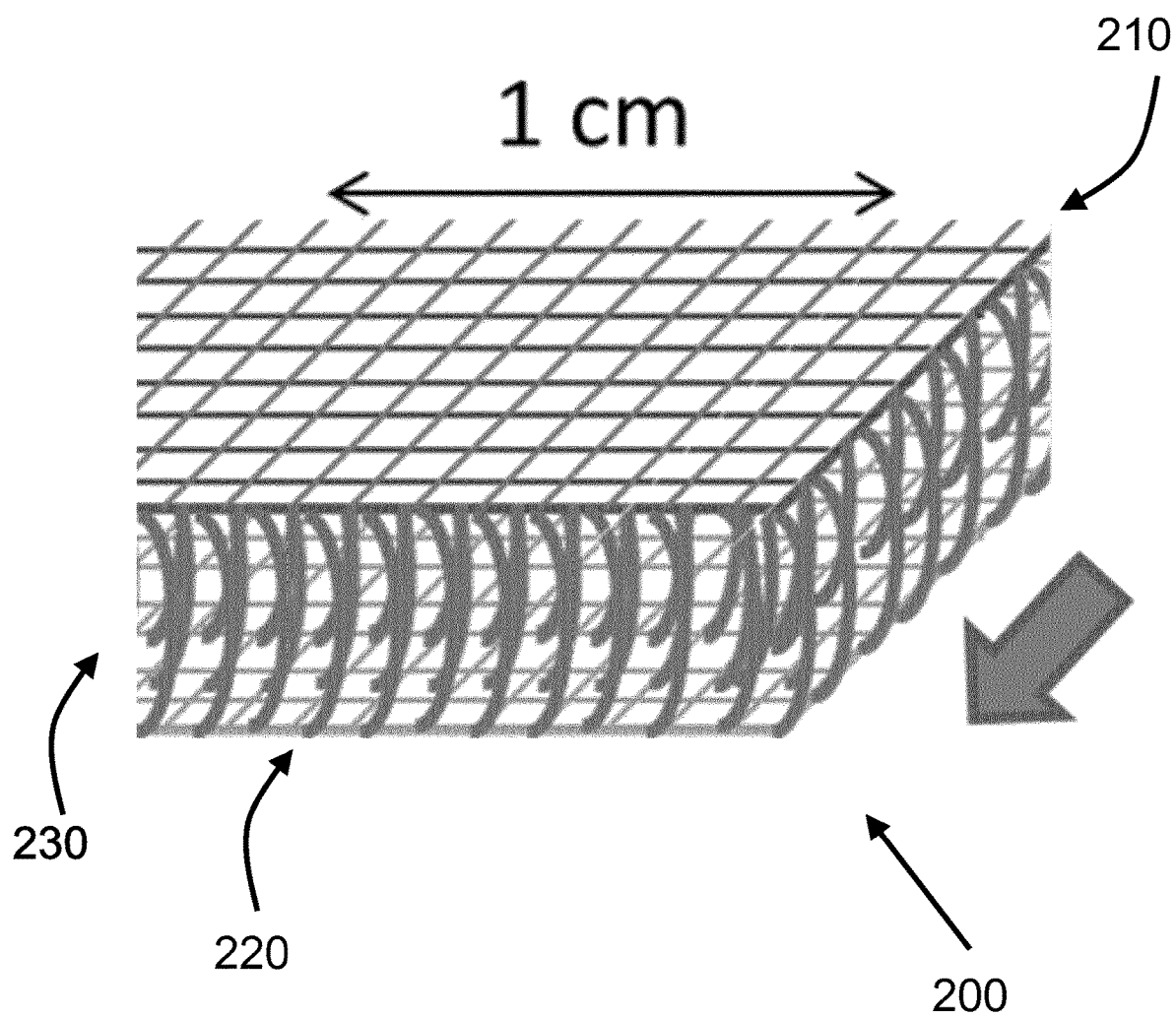

FIG. 2 shows according to an exemplary embodiment of the invention a spacer network of filaments 200 of the artificial cartilage. The spacer network of filaments 200 shows a top surface layer 210, a bottom surface layer 220, and filaments crossing in a middle area layer 230 between both the top and bottom surface layers limiting and restricting the maximum distance between both the top and bottom surface layers. The spacer network of filaments 200 shows a course density of about 10 for the top surface layer 210, given that the horizontal direction is the course direction, and the arrow indicates the wale direction.

Figure 3:
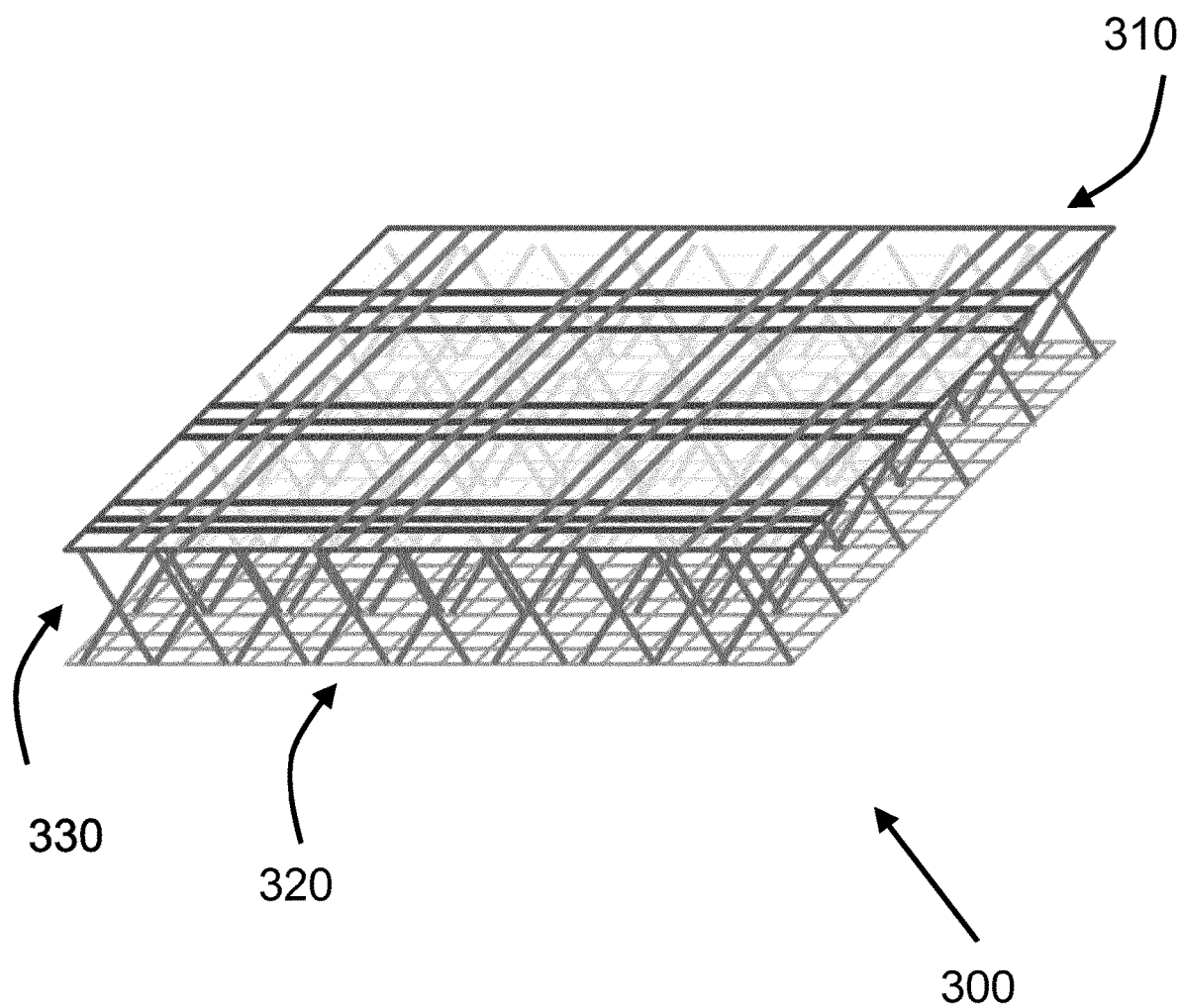

FIG. 3 shows according to an exemplary embodiment of the invention a spacer network of filaments 300 of the artificial cartilage. The spacer network of filaments 300 shows a top surface layer 310, a bottom surface layer 320, and filaments crossing in a middle area layer 330 between both the top and bottom surface layers limiting and restricting the maximum distance between both the top and bottom surface layers. This example further shows the spacer network of filaments 300 with a macroporous top surface layer 310 to a microporous bottom surface layer 320 (macro- and micro-porous are defined by the spacing between the filaments and relative to each other). The piles of filaments in the middle area layer 330 is tilted 60 degrees relative to either the top or bottom surface layer.

Figure 4:
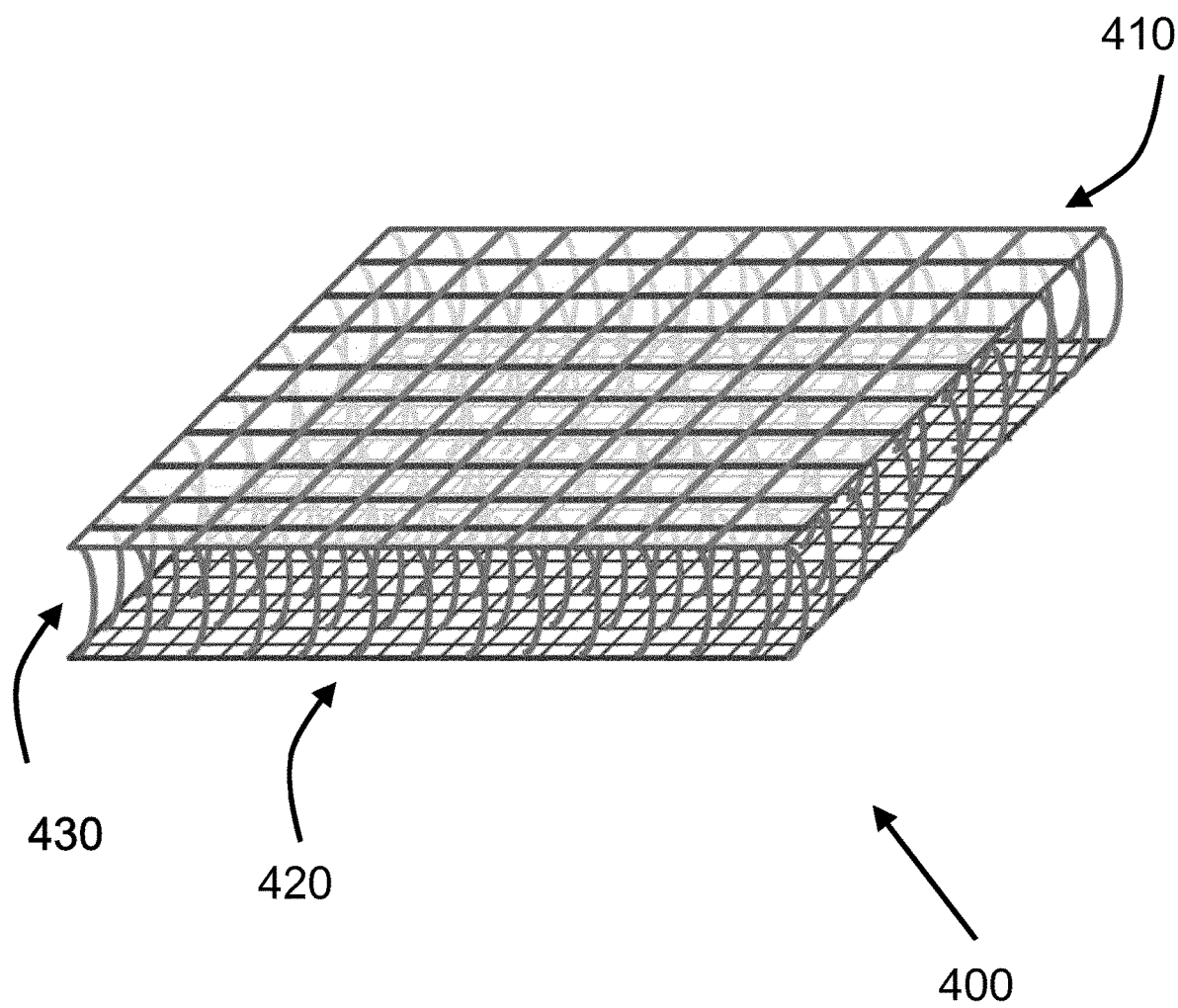

FIG. 4 shows according to an exemplary embodiment of the invention a spacer network of filaments 400 of the artificial cartilage. The spacer network of filaments 400 shows a top surface layer 410, a bottom surface layer 420, and filaments crossing in a middle area layer 430 between both the top and bottom surface layers limiting and restricting the maximum distance between both the top and bottom surface layers. This example further shows the spacer network of filaments 400 with different porosities (filament densities) in the top surface layer 410 and bottom surface layer 420.

Figure 5:
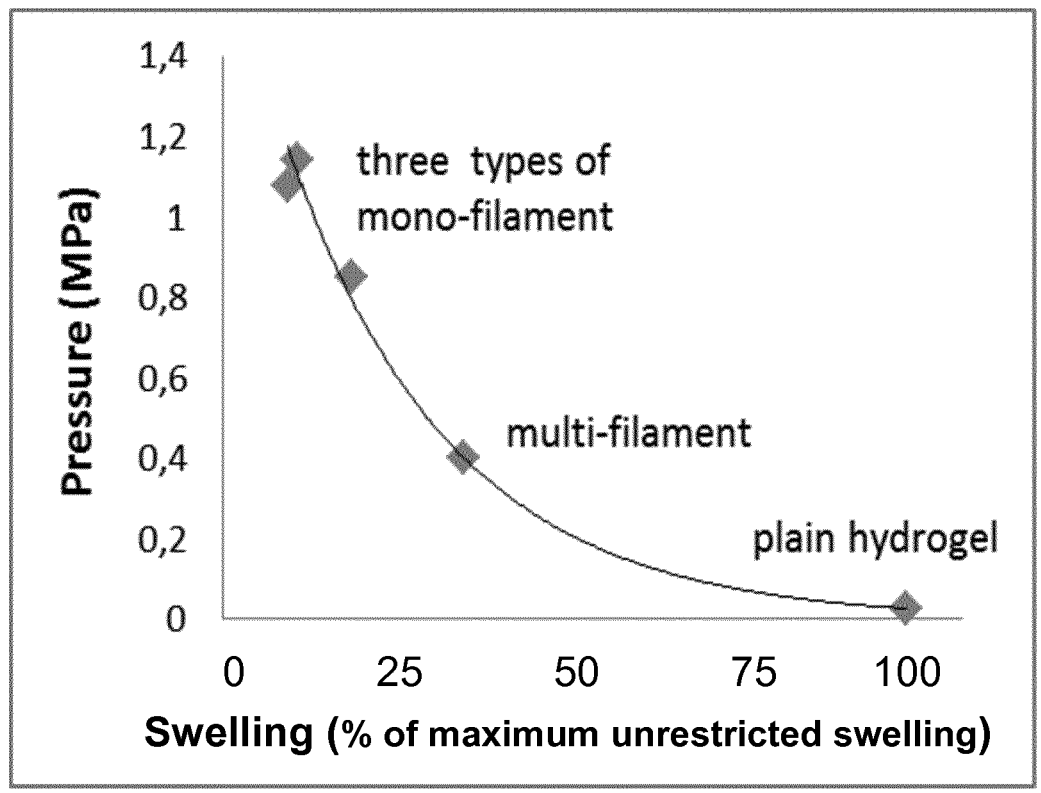

FIG. 5 shows according to an exemplary embodiment of the invention, in which the construct gains compressive load-carrying capacity when a spacer network of filaments is used to restrict the swelling of a hydrogel between the top and bottom surface layers, i.e. defined as "artificial cartilage". When unrestricted, i.e. fully swollen=100%, the hydrogel crumbled at pressures as low as 0.03 MPa, but when restricted to 10% of it swelling capacity, by the spacer network of filaments, the artificial cartilage held more than 1 MPa, without failure, equal to the physiological loading range of natural cartilage.

Figure 6:
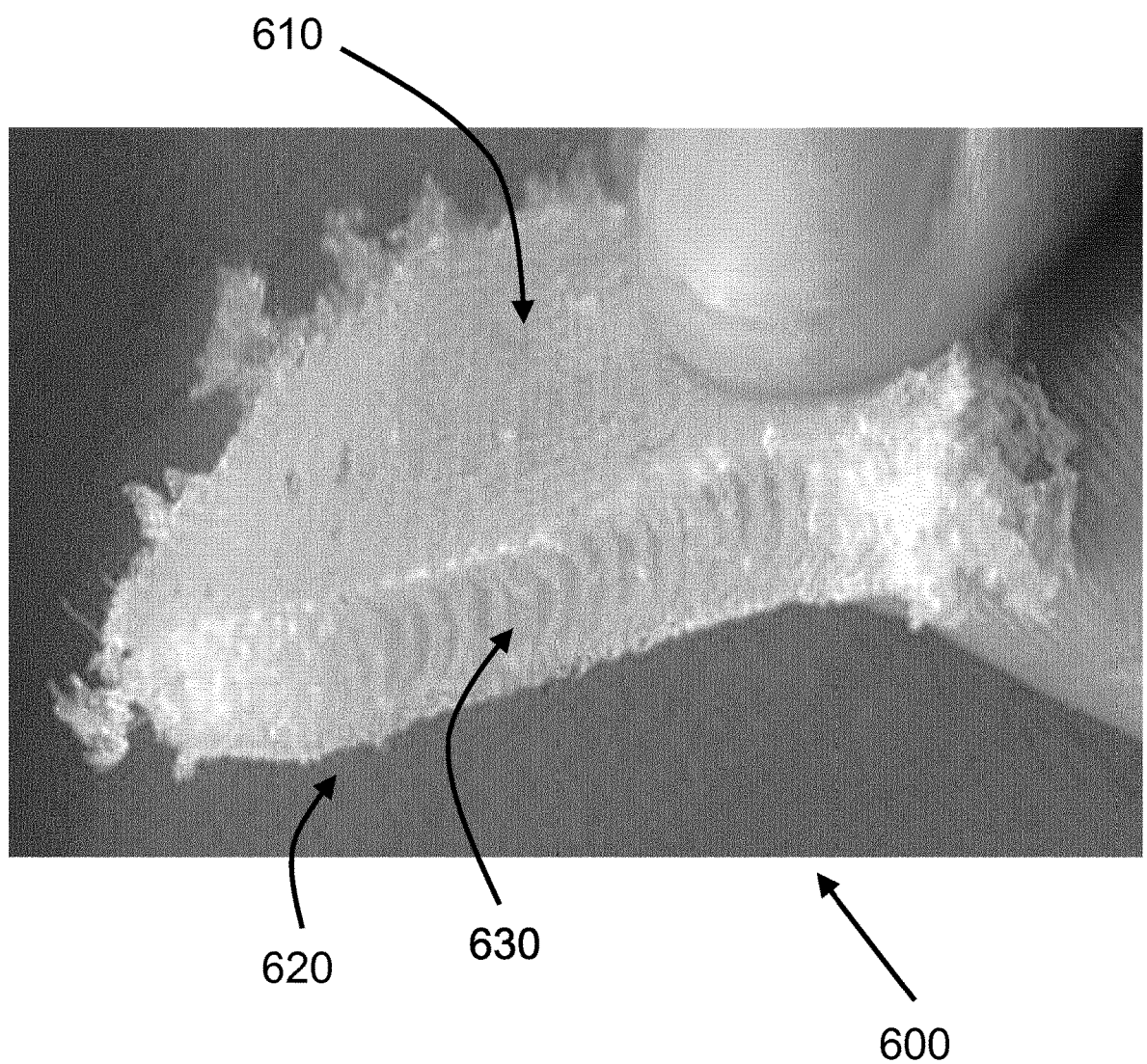

FIG. 6 shows according to an exemplary embodiment of the invention a construct of the artificial cartilage (cut in half) that was compressed until 1.14 MPa. In this example, as a proof of concept, no attention was put in the design to the edges as it can be seen that the peripheral hydrogel edges show crumbling. However, the core of the hydrogel in the middle area and restricted by the spacer fabric was still intact after this excessive loading. In this example, the artificial cartilage 600 shows a fixed negative charged hydrogel infused within the restrictive swelling spacer network. The artificial cartilage 600 shows a top surface layer 610, a bottom surface layer 620, and filaments crossing in a middle area layer 630 between both the top and bottom surface layers limiting and restricting the maximum distance between both the top and bottom surface layers, and restricting the swelling of the fixed negative charged hydrogel.

DETAILED DESCRIPTION

It is important to note that compared to the effects of regular enhancement of hydrogels with reinforcing fibers, the principal of load-bearing in the artificial cartilage is quite different. Regular fiber-reinforced hydrogels exhibit enhanced stiffness when loaded, because the reinforcing fibers are stretched together with the deforming hydrogel. The stretching of the stiffer fibers enhances the stiffness of the composite. This stiffness enhancement is also present when the construct is compressed if fibers are oriented such that they experience shear and tensile stress components of the full stress tensor. In contrast, the load-bearing mechanism of the artificial cartilage is not the result of straining of the reinforcing fibers under external loading. Rather, the enhanced stiffness is already obtained prior to loading and is derived from the swelling capacity of the hydrogel. The hydrogel with fixed negative charges that has been infused within the restrictive swelling spacer network is limited/restricted in its swelling capacity by the spacer filament network. The result is a swelling potential, which provides the artificial cartilage with its load-bearing function. In other words, the artificial cartilage is not a fiber-reinforced hydrogel, but a fiber-network restricted swelling hydrogel, specifically aiming at maintaining a certain swelling potential of the hydrogel.

Mechanical Load-Bearing Mechanism

When a material carries a weight, it means that the internal stresses inside the material balance the externally applied load. These stresses develop in elastic materials as a result of deformation of the material. This is the natural way in which metallic or polymeric implants carry the applied load in a joint. In addition to these stresses induced by material deformation, any other type of internal stress may contribute to load-bearing. For example, load-bearing in an air-mattress is carried by the air pressure inside the mattress.

The present invention uses a stress that will be referred to as 'osmotic swelling potential' or 'restricted osmotic swelling' as the stress that counterbalances the mechanical load in a joint. Osmotic pressure is the measure of the potential of a solution to take in water by osmosis. This is driven by a difference in the number of dissolved particles in two adjacent solutes. When a polymer or hydrogel with (positively or negatively) charged groups is placed in water, the charged groups will collect counter-ions. The larger the density of charged groups, the larger the density of counter-ions, the larger the osmotic pressure in the material and the stronger its potential to take in water.

If a material is allowed to swell freely and becomes fully saturated with water, it loses its osmotic swelling pressure and does not attract more water. In contrast, if the osmotic pressure difference is driving fluid to flow into the material, but swelling of the material is prohibited, then the material would not significantly increase in size and the osmotic swelling pressure is captured inside the material as an osmotic swelling potential.

The power of the osmotic swelling potential that develops when osmotic swelling is restricted is very significant, and dominates the load-bearing capacity of healthy natural articular cartilage. However, this mechanism has not yet been used in implants for articular joints. Hydrogels that have been used in cartilage-replacing implants, even those that swell, did not use restricted osmotic swelling as the load-bearing mechanism.

Embodiments of the invention selectively use osmotic pressure generated by restricted osmotic swelling as the mechanism to carry loads in an articulating joint. This is accomplished by combining a hydrogel that contains fixed negative charges, and therefore has an inherent osmotic potential, with a fiber fabric that strongly restricts the swelling of the hydrogel. As a consequence of the inability to swell, the osmotic swelling potential in the hydrogel is unmet, and an osmotic swelling pressure resides inside the hydrogel. This osmotic swelling pressure is employed to balance the loads in the joint. More specific, the implant has two parts (see FIGS. 1-4, 6): 1) a swelling hydrogel (a fixed negative charged hydrogel), and 2) a restrictive swelling network (spacer network of filaments).

The restrictive swelling network is a spacer fabric or a spacer network of filaments. The spacer network of filaments has two parallel tightly knitted or woven surfaces, connected by filaments (pole threads) crossing between them. These filaments limit the maximum distance between the two layers. The spacer network of filaments can also be composed of multiple layers with filaments crossing between each adjacent layer. The swelling hydrogel is interspersed between the parallel layers, within the area of crossing filaments. When the hydrogel starts swelling, the adjacent layers maintain the bulk of the hydrogel between them and the interspersed pole threads stretch to the amount that their tensile stresses together equal the osmotic pressure, resisting further swelling of the hydrogel. Thus, the filaments capture the osmotic swelling potential of the hydrogel, which now contains a high internal osmotic pressure.

For this osmotic pressure to be large enough to carry the loads in an articulating joint, e.g. the knee, the hydrogel and spacer fabric should meet the following criteria.

- At least 60% of the construct volume should be the swelling hydrogel.
- The hydrogel should have a fixed charge density between −0.17 and −0.23 mEq/ml, and with this particular fixed charge density, it should swell to at least 2 times its original volume when placed in physiological saline under free swelling conditions.
- After insertion of the hydrogel into the spacer fabric component, the hydrogel should swell to at most 10% of its maximum swelling capacity under unrestricted, free-swelling conditions to generate enough swelling pressure, or in another embodiment should swell to at most 5% of its maximum swelling capacity under unrestricted, free-swelling conditions to generate enough swelling pressure (FIG. 5).
- The filament density and filament organization (knit or weave construction) should be such that they form parallel layers. This structure that forms the free cartilage surface must prevent the hydrogel from being expelled from the construct through the surface layer upon loading or swelling. This may be achieved by using a closed knit or weave construction in combination with a high knitting or weaving density. The layer that faces the bone may be closed to prevent expelling of the hydrogel, or it may be porous if the supporting material prevents expelling of the hydrogel from the artificial cartilage.
- The course/weft density should be at least 10 courses/wales per centimeter, but densities of 20 or more are preferred. The course/weft density is a machine setting, and the maximum course density is determined by technical limitations of the machine (course/wale direction, see FIG. 2). The wale/warp density, i.e. the fiber density perpendicular to the course/weft direction, should be 6 or more. The present application is not limited to a maximum course/weft or wale/warp density value. The course/weft density is not that important for the final construct, because the exact knitting or weaving patterns in 2D for the top and bottom surfaces will overrule the importance of the density. In addition, there are various possibilities to knit or weave these surfaces, including variations in knitting or weaving density that result in advanced macro-porous structures. The main dominating property relates to the number of fibers crossing between the top and bottom surface (pile density) FIGS. 1-4, 6.
- The filament organization (knit or weave construction) in the knitted or woven superficial layer can be used to create a construct with isotropic or anisotropic properties, i.e. an implant that behaves stiffer in the split-line direction of the cartilage than perpendicular to the split-line direction.
- The tensile properties of the interspersing pole threads and their density must be sufficient to withstand the swelling pressure of the hydrogel. They may be multi-filaments or mono-filaments, and they may either run in parallel, or be organized in any other (criss-cross) pattern. In general, the pile density, i.e. the number of fibers crossing over between the top and bottom layer per $cm^2$ should be least 60 (course/weft density 10 multiplied by wale/warp density 6), but preferably double the density in both directions, i.e. in the order of 240 filaments per $cm^2$. The maximum number of crossing fibers is restricted only by the requirement that at least 60% of the material should be comprised of the swelling hydrogel. A higher density of thinner fibers is preferred to prevent the hydrogel from being squeezed out laterally, through the pole threads.

Adopting a load-bearing mechanism based on restricted osmotic swelling potential for a cartilage implant is a new concept. This includes implants where (swelling) hydrogels are reinforced with a fiber network. Such implants use fibers to reinforce the polymeric hydrogel, increasing their tensile and shear properties, but do not use the fiber networks to generate osmotic swelling as the main load-bearing mechanism in the construct.

Tailoring of Load-Bearing Properties

The approach with the combination of a spacer network of filaments and a hydrogel enables many possibilities to tailor the eventual properties of the implant to meet the patient-specific biomechanical demands. For its application in articular cartilage, the eventual equilibrium stiffness will be 0.5 to 2.0 MPa, to match the stiffness of environmental cartilage in older and younger patients, respectively. In non-equilibrium conditions, the stiffness of the construct will be loading-rate dependent, ranging from 1 MPa during walking to 200 MPa for impact loading conditions.

There are a couple of ways to tune the properties of the construct to meet these demands. They include:

- Tensile properties of the superficial zone in natural cartilage may vary between 100 MPa and 1 MPa for younger (~20 years old) and older (65+ years old) patients, respectively. Modulating these properties can be achieved by varying the knitting or weaving density or the knitting or weaving structure (knit or weave construction), or by selecting a filament with a particular tensile stiffness.

The swelling potential of the hydrogel can be modulated by controlling the number of fixed negative charges per volume of hydrogel. This may be done by modulating the chemical structure of the polymeric network, or by controlling the amount of swelling of the construct between implantation and reaching the unloaded equilibrium state.

Individual filaments, differing in e.g. diameter, stiffness, shape, or the number of filaments in multi-filament constructs, can be chosen for the superficial, the deep, or the interconnecting pole treads, because the knitting or weaving process by which the spacer fabric is created, uses different filaments for each of these layers. This then creates individual properties for these different layers.

Tailoring Other Properties

The properties of the various layers in the spacer network of filaments can be tailored with regard to other properties than stiffness. For example, the articulating layer may be treated to reduce friction with the opposing cartilage surface, the bottom layer may be treated or modulated to enable osseous anchorage and/or promote osseous ingrowth, the intermediate layer may be modulated to enhance binding with the hydrogel.

This tailoring may either be applied:

after the spacer network of filaments is produced though any coating, dipping or spraying process, to the different filaments that end up in the top, bottom and intermediate layers, prior to the knitting or weaving process.

Dimensions and Shape

The thickness of the cartilage replacing implant ranges between 0.8 and 6 mm, depending on the site of application and the thickness of the patient's cartilage. If an osseous core for anchorage is added, the dimensions of such anchorage add to the aforementioned thickness of the chondral part.

The spacer fabric can be cut to the size of the lesion prior to implantation, during the operation. This is a great asset of the present approach over available implants, where the defect needs to be adjusted to the predefined size of the construct.

The spacer fabric is flexible. Therefore, it will naturally follow the curvature of the joint surface that is to be reconstructed. The surface dimensions of the implant are unlimited and may range from anything between a few $mm^2$ to the size of the entire joint surface.

Regeneration

The hydrogel and/or the fiber mesh may either be inert or bioresorbable.

Inert materials may be used for older patients with limited repair capacity (over 50 years). This creates a permanent, immediately load-bearing construct.

Resorbable materials would promote regeneration of native cartilage as the hydrogel resorbs. To promote regeneration, chondrogenic cells, single type or mixture, may be mixed in with the hydrogel upon implantation. The biological tissue that is synthesized by the cells may gradually replace the degrading fibres and/or hydrogel and in this way maintain functionality in the long term.

In a joint, defective cartilage, after removal, and the absence of cartilage may be treated by replacing it with the new biomimetic implant. The artificial cartilage may be initially anchored to the exposed underlying bone and/or glued to the adjacent intact cartilage tissue using existing methods. Two applications methods are envisaged, but the application may not be limited to these approaches:

1. The implant is fully prepared as a hydrogel-filled spacer network of filaments, and implanted as such into the joint. It may be implanted either using a minimally invasive surgical approach, or through open knee surgery.

2. The fibrous spacer fabric may first be fixed in place during a minimally invasive surgical approach or open knee surgery. Subsequently, it is filled with the swelling hydrogel to create the internal swelling pressure.

The new implant, due to its biomimetic construction, allows for immediately load-bearing function while being compliant and mating with the adjacent and opposing cartilage. The articulating surface shall not damage the opposing cartilage because the lubricating nature of the loaded implant: weeping lubrication (poroelastic nature), elastohydrodynamic lubrication (soft compliant nature of implant), and/or if needed boundary lubrication (functional coating of upper fabric sheet). The deeper fabric sheet may be treated to promote bone growth into it permanently anchoring the implant to the underlying bone.

The hydrogel may also be loaded with cells, single type or mixture, to promote regeneration of natural articular cartilage. The main benefit of the artificial cartilage, due to its biomimetic nature, is to allow immediate return of pain free function while promoting cartilage regeneration.

Further extension of the applicability of embodiments of the invention, outside replacing the damaged cartilage in a knee joint:

Replace (damaged) load-bearing cartilage in other joints (including load-bearing joints).

Resurface entire joint surface and replace bearing surface of artificial joints.

Replace non-load-bearing cartilage for cosmetic use in eg. nose, ear.

Replace intervertebral discs.

Application in other load-bearing cases, biological or non-biological:

Support in Shock-absorbing conditions (driver seats, balanced tables for microscopy, or the like).

Applicable in many situations where air cushions are being used at the moment.

What is claimed is:

1. An artificial cartilage, comprising:

a fixed negative charged hydrogel infused within a restrictive swelling network, wherein the restrictive swelling network is a spacer network of filaments with a top surface layer, a bottom surface layer, and some of the filaments crossing in a middle area layer between both the top and bottom surface layers limiting and restricting the maximum distance between both the top and bottom surface layers, wherein the restrictive swelling network restricts the fixed negative charged hydrogel to swell not more than 10% with respect to the maximum swelling capacity of the fixed negative charged hydrogel without being constraint by the restrictive swelling network, wherein the fixed negative charged hydrogel within the restrictive swelling network has an equilibrium stiffness between 0.5 and 2 MPa to resist external loads applied to the top surface layer or the bottom surface layer of the artificial cartilage.

2. The artificial cartilage as set forth in claim 1, wherein at least 60% of the volume of the artificial cartilage is composed of the restricted and swollen fixed negative charged hydrogel.

3. The artificial cartilage as set forth in claim 1, wherein the fixed negative charged hydrogel has a fixed negative charge density of −0.17 to −0.23 mEg/ml and is capable of swelling between 2-15 times compared to the volume of the hydrogel without being restricted.

4. The artificial cartilage as set forth in claim 1, wherein the maximum distance between both the top and bottom surface layers is between 0.8-6 mm.

5. The artificial cartilage as set forth in claim 1, wherein the middle area layer of the spacer network of filaments defines an interconnecting pile of filaments restricting the maximum distance between the top surface layer and the bottom surface layer, with a pile density of at least 10 filaments/cm$^2$, wherein the maximum pile density is limited to ensure at least 60% of the volume of the artificial cartilage is composed of the restricted and swollen fixed negative charged hydrogel, with a pile angle between 45-90 degrees defined with reference to either the top or bottom surface layer, and with an elasticity of the spacer network of filaments between 100 kPa and 10 MPa defined in a load direction perpendicular to either the top or bottom surface layer.

6. The artificial cartilage as set forth in claim 1, wherein the restrictive swelling network restricts the fixed negative charged hydrogel to swell not more than 5% with respect to the maximum swelling capacity of the fixed negative charged hydrogel without being constraint by the restrictive swelling network.

* * * * *